United States Patent [19]

Delgado

[11] Patent Number: 4,641,633

[45] Date of Patent: Feb. 10, 1987

[54] ELECTRONIC SYSTEM FOR THE ACTIVATION, INHIBITION AND/OR MODIFICATION OF THE DEVELOPMENT AND FUNCTIONING OF CELLS, ORGANS AND ORGANISMS OF LIVING BEINGS

[76] Inventor: José M. R. Delgado, Caleruega 21, Madrid, Spain

[21] Appl. No.: 726,922

[22] Filed: Apr. 25, 1985

[30] Foreign Application Priority Data

Mar. 16, 1982 [ES] Spain ................................. 510489

[51] Int. Cl.⁴ .............................................. A61N 1/42
[52] U.S. Cl. ...................................... 128/1.3; 128/1.5
[58] Field of Search ............. 128/1.3, 1.5, 804, 419 L, 128/419 R, 421.3

[56] References Cited

U.S. PATENT DOCUMENTS

| | | | |
|---|---|---|---|
| 703,989 | 7/1902 | Burry | 128/1.5 |
| 2,102,790 | 12/1937 | Drollinger | 128/1.5 |
| 2,103,440 | 12/1937 | Weissenberg | 128/1.3 |
| 3,915,151 | 10/1975 | Kraus | 128/419 F |
| 4,197,851 | 4/1980 | Fellus | 128/422 |
| 4,266,532 | 5/1981 | Ryaby et al. | 128/1.5 |
| 4,402,309 | 9/1983 | Harrison | 128/1.3 |
| 4,428,366 | 1/1984 | Findl et al. | 128/1.5 |

FOREIGN PATENT DOCUMENTS

| | | | |
|---|---|---|---|
| 0039988 | 11/1981 | European Pat. Off. | 128/1.3 |
| 2369850 | 7/1978 | France | 128/1.3 |
| 0676286 | 7/1979 | U.S.S.R. | 128/1.3 |
| 0860767 | 9/1981 | U.S.S.R. | 128/1.3 |

*Primary Examiner*—Edward M. Coven
*Attorney, Agent, or Firm*—Gottlieb, Rackman & Reisman

[57] ABSTRACT

Instrumentation and methodology for the application of non-invasive electromagnetic fields characterized by unidirectional square waves with rising and falling times below 0.1 microseconds and frequencies below 120 pulses per second. The waves are applied through antennas which produce magnetic fields. The magnetic fields are applied to living beings with the purpose of producing predictable modifications of determined structures, functions and manifestations.

21 Claims, 5 Drawing Figures

ELECTRONIC SYSTEM FOR THE ACTIVATION, INHIBITION AND/OR MODIFICATION OF THE DEVELOPMENT AND FUNCTIONING OF CELLS, ORGANS AND ORGANISMS OF LIVING BEINGS

The present invention concerns an electronic system for the activation, inhibition, and/or modification of the development and functioning of cells, organs, and organisms of living beings, applicable from unicellular organisms up to human beings.

The above mentioned system is based on the generation and application of local electrical fields, induced remotely by electromagnetic means, with biological effects which depend on the programming and on pre-selected parametric characteristics.

Since 1947 the inventor and some of his collaborators have performed and published a large series of experiments to investigate morphological, physiological, and pathological effects produced in cells, organs, and organisms of different animal species from bacteria and insects up to humans, produced by electrical stimulae of special characteristics, applied directly or by electromagnetic induction. Results of these investigations have been published successively through the years to describe each new discovery.

The following provides a list of some of these investigations published by the inventor:

Reference 1: Delgado, J. M. R. and R. B. Livingston. SOME RESPIRATORY, VASCULAR AND THERMAL RESPONSES TO STIMULATION OF ORBITAL SURFACE OF FRONTAL LOBE. J. Neurophysiol., 11:39-55, 1948.

Reference 2: Mihailovic, L. and J. M. R. Delgado. ELECTRICAL STIMULATION OF MONKEY BRAIN WITH VARIOUS FREQUENCIES AND PULSE DURATIONS. J. Neurophysiol., 19:21-36, 1956.

Reference 3: Delgado, J. M. R. MULTICHANNEL TRANSDERMAL STIMULATION OF THE BRAIN. Tech. Doc. Rep. #ARL-TR-70-1. Holloman AFB, New Mexico, 24pp. 1970.

Reference 4: Delgado, J. M. R. PHYSICAL CONTROL OF THE MIND: TOWARD A PSYCHOCIVILIZED SOCIETY. Vol. XLI, World Perspectives Series, R. N. Anshen (Ed.), New York: Harper & Row, 280pp., 1969.

Reference 5: Delgado, J. M. R. RADIOCOMMUNICATION WITH THE BRAIN. (10p. brochure for exhibit). Gold Medal Award, Amer, Psychiat. Assoc. Meeting, May 3-6, Washington, D.C., 1971.

Reference 6: Delgado, J. M. R. COMMUNICATION WITH THE CONSCIOUS BRAIN BY MEANS OF ELECTRICAL AND CHEMICAL PROBES. Pp. 25-40 in: "Biological Diagnosis of Brain Disorders". Proc. V. int. Conf. on the Future of Brain Sciences. New York: Spectrum-Wiley, 1973.

Reference 7: Delgado, J. M. R., V. Lipponen, G. Weiss, F. del Pozo, J. L. Monteagudo, and R. McMahon. TWO WAY TRANSDERMAL COMMUNICATION WITH THE BRAIN. Amer. Psychologist, 30:265-273, 1975.

Reference 8: Delgado, J. M. R. TRANSDERMAN COMMUNICATION WITH THE BRAIN IN ANIMALS AND MAN. Invited lecture, XXVI int. Congr. physiol. Sci., New Delhi, October, 1974. Proc. int. Union physiol. Sci. XI: 27, 1974.

Reference 9: Delgado, J. M. R. NEW ORIENTATIONS IN BRAIN STIMULATION IN MAN. Pp. 481-503 in: "Brain-Stimulation Reward", Proc. 1st int. Conf., A. Wauquier and E. T. Rolls (Eds.), Amsterdam North Holland Publ. Co., 622 pp., 1976.

Reference 10: Delgado, J. M. R. INSTRUMENTATION, WORKING HYPOTHESES, AND CLINICAL ASPECTS OF NEUROSTIMULATION. Appl. Neurophysiol., 40:88-110, 1977/78.

Reference 11: Delgado, J. M. R., J. L. Monteagudo, M. Garcia Gracia and J. Leal. TERATOGENIC EFFECTS OF WEAK MAGNETIC FIELDS. IRCS med. Sci., 9:392, 1981.

Reference 12: Delgado, J. M. R., J. Leal, J. L. Monteagudo and M. Garcia Gracia. EMBRYOLOGICAL CHANGES INDUCED BY WEAK, EXTREMELY LOW FREQUENCY ELECTROMAGNETIC FIELDS. J. Anat., 134:533-551, 1982.

Reference 13: Delgado, J. M. R., J. Leal, A. Parreno, M. Garcia Gracia and J. L. Monteagudo. DIOLOGICAL EFFECTS OF WEAK ELECTROMAGNETIC FIELDS. En Proc. 5th Europ. Neurosci. Conf. Liege, September, 1981.

Reference 14: Monteagudo, J. L., M. Garcia Gracia, J. Leal, C. Hernandez-Ros, E. Ramirez, J. Ortega Klein, J. Palacios Carvajal y J. M. R. Delgado. APLICACION BIOMECANICA DE ESTIMULOS MAGNETICOS. Abstr. en Proc. IV Simp. Soc. iber. Biomecanica, Valencia, November, 1981.

Reference 15: Garcia Gracia, M., J. L. Monteagudo, E. Ramirez and J. M. R. Delgado. ELECTROMAGNETIC MODIFICATIONS OF THE BRAIN. In Proc. 1st World Congr. IBRO, Lausanne, April, 1982.

Reference 16: Leal, J., A. Ubeda, A. Trillo, J. L. Monteagudo and J. M. R. Delgado. MODIFICATION OF EMBRYOGENESIS BY MAGNETIC FIELDS. In Proc. 1st World Congr. IBRO, Lausanne, April, 1982.

Reference 17: Ubeda, A., M. A. Jimenez, M. A. Trillo, J. Leal, and J. M. R. Delgado. FAVORABLE AND TERATOGENIC EFFECTS OF ELECTROMAGNETIC FIELDS ON CHICK EMBRYOGENESIS. In Proc. EDBO Conf., Strasburg, June, 1982.

Reference 18: Delgado, J. M. R. ELECTROMAGNETIC EFFECTS: FROM INSECTS TO HUMANS. In Proc. Symposium on "Biomagnetism in Psychophysiology" 1st. Int. Conf. on Psychophysiology, Montreal, August, 1982.

Reference 19: Ramirez, E., J. L. Monteagudo, M. Garcia Gracia and J. M. R. Delgado. ELECTROMAGNETIC EFFECTS IN DROSOPHILA. In Proc. 6th Europ. Neurosci. Congr., Torremolinos, September, 1982.

Reference 20: Paino, C. L. and J. M. R. Delgado. RUNWAY PERFORMANCE MODIFIED BY ELECTROMAGNETIC FIELDS. In Proc. 6th Europ. Neurosci. Congr., Torremolinos, September, 1982.

One of the objectives of all these studies has been the activation, inhibition, and modification of cells and organisms by means of their electrical stimulation which may be programmed and applied by remote control through the intact skin in such a way that different effects have been obtained by choosing different, specific electrical parameters.

The importance of codification of signals and parameters of electrical currents to obtain specific biological effects was studied and demonstrated by the inventor and others in the above identified References 1 and 2. Many of these findings are summarized in the above Reference 4. In the recent published investigations referred to above References 12 and 18, there has been shown that some parameters of electromagnetic waves may have detrimental teratogenic effects. These references show the importance of the shape of the magnetic waves in producing beneficial results. It is shown in these references, that it is essential to have suitable experimental knowledge about which parameters have beneficial, neutral or detrimental effects.

All this previous research led to the development and construction of the system which is the object of the invention, constituting a new system in its electronics, biological effects, and possible scientific and therapeutic applications.

The system, developed according to the invention, consists of a generator of signals produced electronically and one or several antennas which radiate electromagnetic energy over a tissue or biological organism.

The use of electromagnetic coils applied to the skin for transdermal stimulation of tissues, and retaining methods for this purpose, are described in great detail in the above identified references. These include studies performed on monkeys, chimpanzees, and in human patients. These are described in the above identified References 4, 3, 5, 7, 9 and 9.

It should be emphasized that the use of inductive coils to provide electrical current is not new. The use of two coils separated by a distance smaller than their diameter constitutes the configuration known as "Helmholz coils", honoring the memory of the illustrious German physics professor, H. L. F. von Helmholtz (1821–1894) who studied the properties of these coils which from his time have been described in many textbooks on electricity.

The following is a detailed description of the system, illustrated with drawings and presented as orientation, not as limitation of the system.

Figure 1:
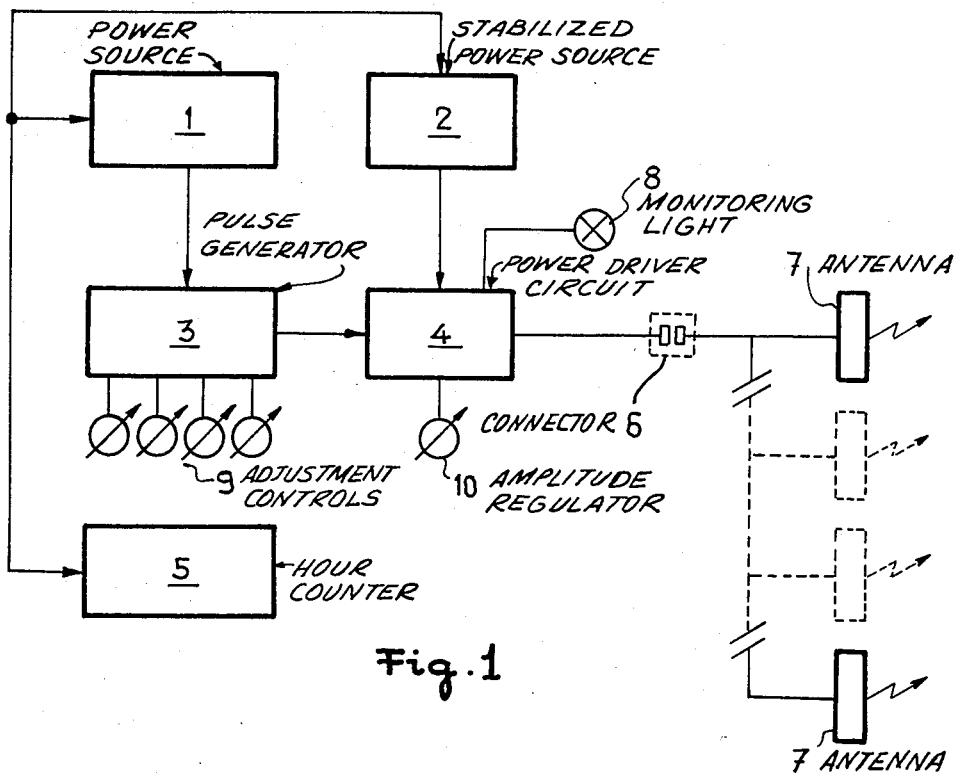
FIG. 1 shows the block diagram representing the system of the invention.

With reference to FIG. 1, power is obtained from the commercial electrical line of 117 V/60 Hz (or 220 V/50 Hz) which is transformed by the power source (1) providing a continuous tension stabilized at a low level in order to feed the circuits of the digital generator (3). These circuits are provided with four controls (9) which allow the adjustment of the timing of the series of generated impulses. The output of the digital impulses shaped by the generator (3) activate a power excitator (4) which is fed by a stabilized power source (2) designed to regulate the amplitude of the pulses sent to the connector (6). This connector (6) allows the mechanical and electrical connection with one or several antennas (7).

The block diagram also has an hour counter (5), an amplitude regulator (10), and a monitoring light (8).

Figure 3:
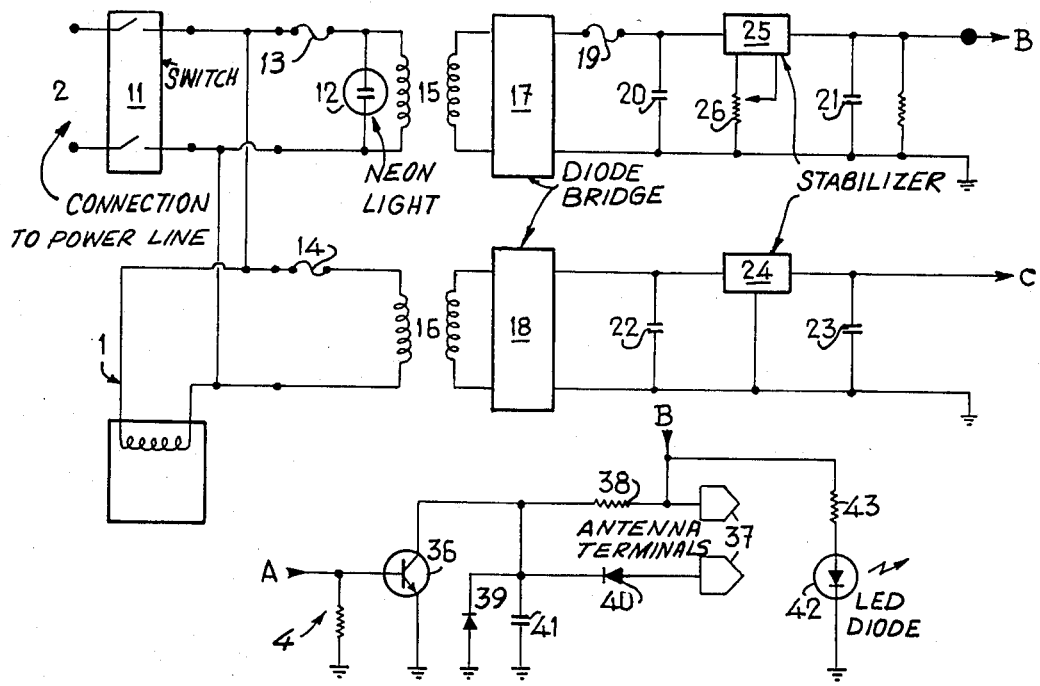
FIG. 3 shows the general electronic circuit which generates the excitation.
Figure 3:
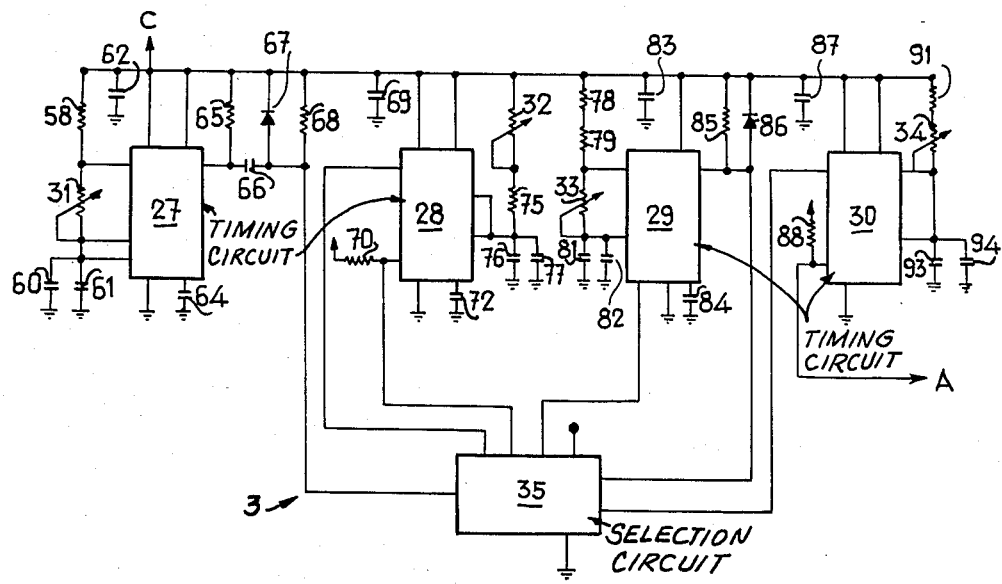

The electronic circuits are described in greater detail with reference to FIG. 3. The switch (11) allows the general on and off connection of the instrument to the power line. The neon light (12) indicates the existence of power line tension; the fuses (13 and 14) protect the input circuit of the transformers (15 and 16). Two diode bridges (17 and 18) provide rectification of the input sinusoidal wave. The fuse (19) is an additional protection for the power source circuit (2). Tension is filtered with the help of condensers (20,21,22,23). The power source (2) provides a fixed voltage stabilized by integrated circuit (25) and may be adjusted by a special potentiometer (26). This possible adjustment permits voltage control of the signal which excites the antennas. An integrated circuit (24) permits stabilization of the voltage provided by the power source (1).

The integrated circuits (27,28,29 and 30) in coordination with the associated resistances and condensors (58, 60, 61, 62, 64, 65, 66, 67, 68, 69, 70, 72, 75, 76, 77, 78, 79, 81, 82, 83, 84, 85, 86, 87, 88, 91, 93, 94) permit the establishment of the basic timing for the shaping of stimulation pulses, which may be regulated by the resistances (31,32,33, and 34). The integrated circuit (35) provides the logic functions for adjustments between the timing circuits in order to generate the chosen electrical signals.

The final logic output from the integrated circuit (30) activates the power transistor (36) which is the final stage for excitation of the antennas connected through the terminals (37). The resistance (38) absorbs the residual energy. The diodes (39 and 40), together with the condenser (41), constitute a protective mechanisms for the final transistor (36). The solid state light (LED diode) (42) is polarized by resistance (43) to provide a light signal synchronous with the power pulse given to the antenna. This light will provide an objective indication of malfunction.

Figure 4:
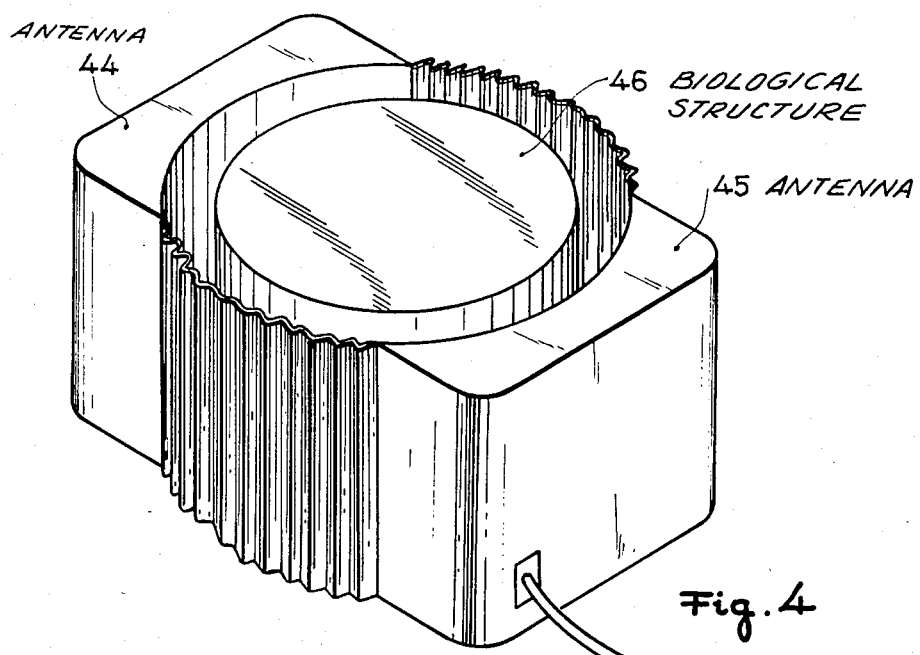
FIGS. 4 and 5 show the application of the system in one example of therapy in tissues and organs of a human patient.
Figure 5:
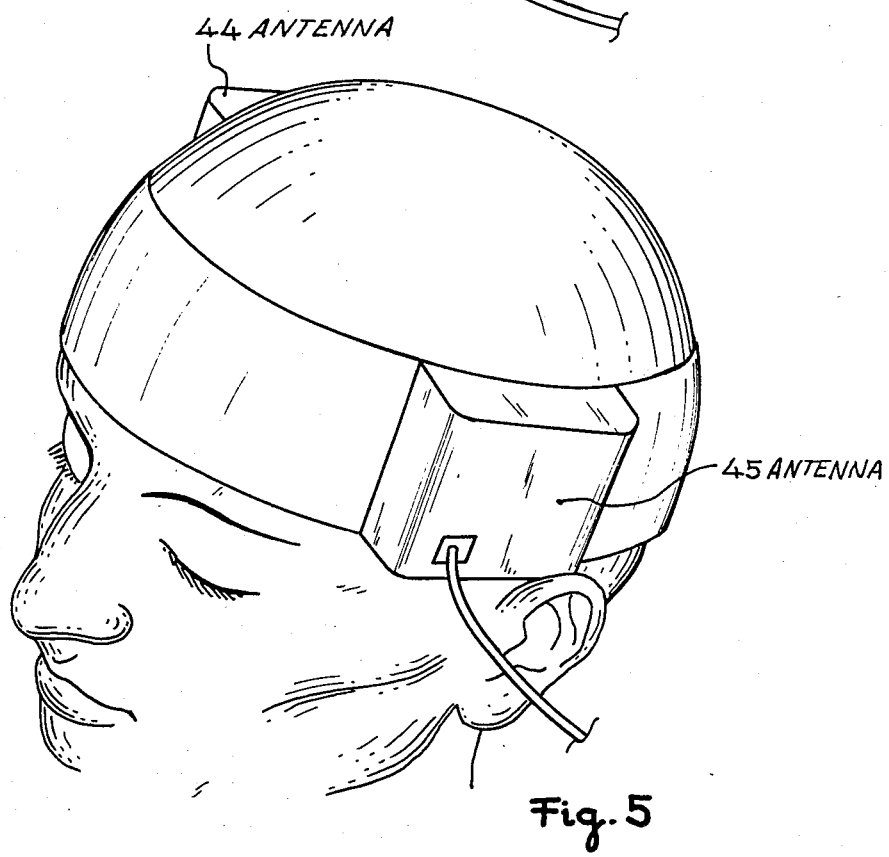

FIG. 4 presents a typical application of the system with two synergic square antennas (44 and 45) radiating energy over a biological structure (46) which may be a tissue, an organ, or organism. FIG. 5 shows specifically a case of therapeutic application of the system to the head. In this case, two square antennas (44 and 45), synergically excited, are placed on an elastic bandage, fixing them over a determined part of the head with the electromagnetic field reaching skin, bone, and brain. This type of therapy may be applied to a variety of tissues and organs in human patients and may be used over surgical dressing, bandages, and casts. With suitable, determined parameters of stimulation, local tissue infections can be reduced and by using other stimulation parameters, cellular development and calcification of broken bones may be accelerated. In other cases, tissue grafts, nerve repair, local chemistry, physiological activities, and other processes may be influenced and improved.

Research supporting the application of electromagnetic radiation has been conducted in Drosophila, snails, crabs, fish, mice, rats, cats, chick embryos and monkeys, and also includes therapeutic applications to human patients. Studies have involved unitary neuronal activity, electrical activity of the cerebellum, biological viability, embryological development, spatial orientation, motility, brain chemistry, pregnancy, conditioning, free behavior and sleep-wakefulness. Additional studies have involved bone healing in rats and human patients. These are described in the above identified References 11, 12, 13, 14, 15, 16, 17, 18, 19 and 20.

The cumulative hour counter with numeric visualizaion (5) provides a precise and permanent control of the applied dose of electromagnetic radiation. The monitoring light (8) indicates that the electronic equipment is working, supplying the prescribed therapy.

Figure 2:
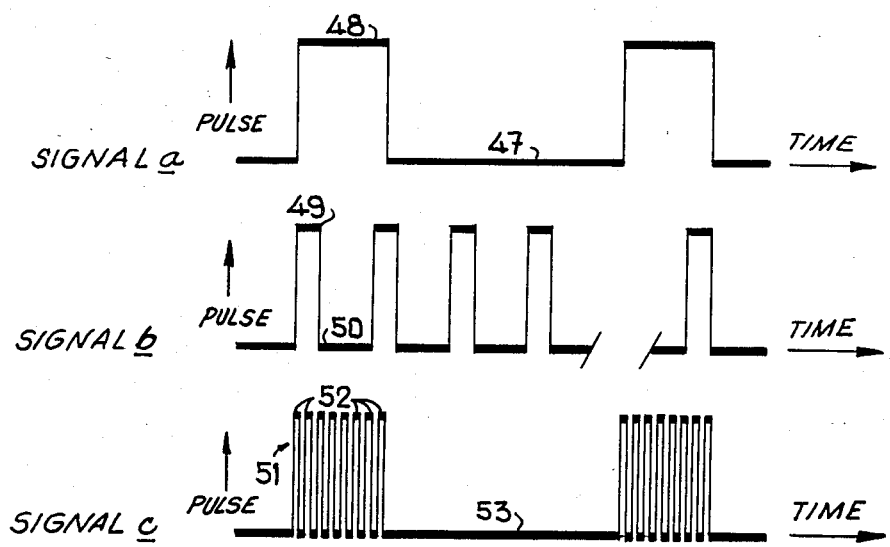
FIG. 2 shows the shape of the waves of electrical voltage generated by the electronic circuits which excite the antennas.

The drawing of FIG. 2 illustrates the pattern of signals generated by the electronic circuits for excitation of the antennas. Three types (a,b, and c) are used. Signal a is a regular succession of rectangular impulses in which time (47) is always greater than time (48). These pulses are very sharp, with rising and falling time of less than 0.1 microsecond. Duration of (48) is adjustable between 1 and 120 pulses per second. Signal b is a regular succession of rectangular impulses grouped as trains with repeat rates between 10 milliseconds and 10 seconds. Times (49) and (50) are adjustable in the same range as (47) and (48). The number of pulses which form each train may vary between two and one hundred.

The third type of signal, c, is formed by a high frequency component (51), between 10 Kilohertz and 100 Megahertz, modulated at 100% by a rectangular envelopment whose temporal characteristics (52) and (53) can be regulated with the same values as (47) and (48) respectively.

In summary, by means of the described system and based on our experience accumulated since 1947, we can influence cells, organs, and organisms of different species, and these applications include scientific investigations and therapeutic use, based as already explained on the production of local electrical fields induced by externally applied electromagnetic fields of specific characteristics.

The inventor reserves the rights to introduce in the present invention any improvements which could be legally acceptable.

What is claimed is:

1. An electromagnetic system for non-invasive modification of living cells and organisms, comprising:
   electronic generator means for generating very stable, unidirectional, symmetrical square waves, and including means for adjusting the timing of said square waves to provide very sharp square waves having rise times and fall times each of less than 0.1 microsecond; and
   at least one antenna means for receiving said square waves and producing magnetic fields which can be applied to the living cells and organisms to modify their morphological and functional characteristics without disturbance of the cellular membrane protecting the cell and organism.

2. An electromagnetic system as in claim 1, wherein said electronic generator means comprises means for producing a high frequency component signal of between 10 Kilohertz and 100 Megahertz, said high frequency signal being modulated by said square waves.

3. An electromagnetic system as in claim 1, wherein the frequency of said square waves is less than 120 pulses per second.

4. An electromagnetic system as in claim 1, wherein said square waves are grouped as repetitive pulse trains having repetition rates between 10 milliseconds and 10 seconds, and the number of pulses in each pulse train varies between two and one hundred.

5. An electromagnetic system as in claim 1, further comprising time counter means coupled to said generator means for monitoring the time and duration of application of the magnetic field.

6. An electromagnetic system as in claim 1, wherein said generator means comprises a plurality of integrated circuit timing devices for producing said square waves, and an integrated circuit logic selection circuit for providing selection of said square waves in a single, repetitive or grouped arrangement and for direct application as well as a modulating application of said square waves.

7. An electromagnetic system as in claim 1, and further comprising a first power source for providing a first rectified power output to said generator means, a second power source for providing a second rectified power output, regulator means for controlling the level of the second rectified power output, and a power driver circuit receiving the output from said generator means and said second rectified power output, the output from said power driver circuit being applied to said at least one antenna means.

8. An electromagnetic system as in claim 1, wherein said antenna means comprises two square antennas, and a continuous cylindrical elastic material supporting said square antennas.

9. An electromagnetic system as in claim 1, wherein said antenna means comprises a plastic housing having a central bore for receiving a living organism, and a pair of square antennas embedded in the plastic material of said housing in diametrically opposed positions with respect to said central bore.

10. A method of non-invasive modification of living cells and organisms, comprising applying an antenna non-invasively with respect to the organism, applying to the antenna very stable, unidirectional, symmetrical and very sharp electrical square waves with rising and falling times each of less than 0.1 microsecond to cause the antenna to produce a magnetic field which penetrates into the organism without disturbing the cellular membrane of the organism.

11. The method of claim 10, wherein the square waves applied to the antenna modulate a high frequency signal of between 10 Kilohertz and 100 Megahertz.

12. The method of claim 10, wherein the square waves have a frequency less than 120 pulses per second.

13. The method of claim 10, wherein the square waves are grouped as repetitive pulse trains having repetition rates between 10 milliseconds and 10 seconds, and the number of pulses in each pulse train varies between two and one hundred.

14. An electromagnetic system for non-invasive bone growth stimulation, comprising:
   electronic generator means for generating very stable, unidirectional, symmetrical square waves, and including means for adjusting the timing of said square waves to provide very sharp square waves having rise times each and fall times of less than 0.1 microsecond; and
   at least one antenna means for receiving said square waves and producing magnetic fields which can be applied to living bone to modify its morphological and functional characteristics without disturbance of the bone structure.

15. An electromagnetic bone growth stimulation system as in claim 14, wherein said electronic generator means comprises means for producing a high frequency component signal of between 10 Kilohertz and 100 Megahertz, said high frequency signal being modulated by said square waves.

16. An electromagnetic bone growth stimulation system as in claim 14, wherein the frequency of said square waves is less than 120 pulses per second.

17. An electromagnetic bone growth stimulation system as in claim 14, wherein said square waves are grouped as repetitive pulse trains having repetition rates between 10 milliseconds and 10 seconds, and the number of pulses in each pulse train varies between two and one hundred.

18. A method of non-invasive bone growth stimulation, comprising applying an antenna non-invasively with respect to living bone, and applying to the antenna very stable, unidirectional, symmetrical and very sharp electrical square waves with rise times and fall times each of less than 0.1 microsecond to cause the antenna to produce a magnetic field which penetrates into the bone without disturbing the bone structure.

19. The bone growth stimulation method of claim 18, wherein the square waves applied to the antenna modulate a high frequency signal of between 10 Kilohertz and 100 Megahertz.

20. The bone growth stimulation method of claim 18, wherein the square waves have a frequency less than 120 pulses per second.

21. The bone growth stimulation method of claim 18, wherein the square waves are grouped as repetitive pulse trains having repetition rates between 10 milliseconds and 10 seconds, and the number of pulses in each pulse train varies between two and one hundred.

* * * * *